United States Patent
Yun et al.

(10) Patent No.: US 10,346,601 B2
(45) Date of Patent: Jul. 9, 2019

(54) BIOMETRIC INFORMATION ACQUISITION METHOD AND DEVICE FOR SAME

(71) Applicant: SAMSUNG ELECTRONICS CO., LTD., Suwon-si (KR)

(72) Inventors: In-kuk Yun, Suwon-si (KR); Je-in Yu, Seoul (KR); Dae-kwang Jung, Suwon-si (KR); Jun-ho Koh, Yeongtong-gu (KR); Byeong-hoon Kwak, Uiwang-si (KR); Sung-chan Kim, Suwon-si (KR); Chang-han Kim, Suwon-si (KR); Hyun-jung Kim, Suwon-si (KR); In-hak Na, Yongin-si (KR); Kang-jin Yoon, Seoul (KR); Yong-chan Lee, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 2 days.

(21) Appl. No.: 15/562,026

(22) PCT Filed: Mar. 4, 2016

(86) PCT No.: PCT/KR2016/002193
§ 371 (c)(1),
(2) Date: Sep. 27, 2017

(87) PCT Pub. No.: WO2016/159523
PCT Pub. Date: Oct. 6, 2016

(65) Prior Publication Data
US 2018/0096119 A1  Apr. 5, 2018

(30) Foreign Application Priority Data
Mar. 27, 2015 (KR) .......... 10-2015-0043296

(51) Int. Cl.
*G06F 21/32* (2013.01)
*A61B 5/024* (2006.01)
(Continued)

(52) U.S. Cl.
CPC ............. *G06F 21/32* (2013.01); *A61B 3/14* (2013.01); *A61B 5/0077* (2013.01); *A61B 5/024* (2013.01);
(Continued)

(58) Field of Classification Search
CPC ............. G06F 21/32; A61B 3/14; A61B 5/02; A61B 5/024; G06Q 20/40145; G06Q 20/382; G07C 9/00158
(Continued)

(56) References Cited

U.S. PATENT DOCUMENTS 4,063,551 A  12/1977  Sweeney
8,048,065 B2  11/2011  Grecu et al.
(Continued)

FOREIGN PATENT DOCUMENTS

KR  1020020078225 A  10/2002
KR  100691172 B1  3/2007
(Continued)

OTHER PUBLICATIONS

International Search Report and Written Opinion, issued by International Searching Authority in corresponding International Application No. PCT/KR2016/002193, dated May 30, 2016 (PCT/ISA210 & PCT/ISA/237).
(Continued)

*Primary Examiner* — Amandeep Saini
(74) *Attorney, Agent, or Firm* — Sughrue Mion, PLLC

(57) ABSTRACT

A method for a device to acquire biometric information includes acquiring a plurality of images including an ocular region using an infrared ray (IR) image sensor, detecting a
(Continued)

sclera region in each of the plurality of acquired images, sensing a change of the detected sclera region, and determining biometric information based on information on the sensed change of the sclera region.

11 Claims, 18 Drawing Sheets

(51) Int. Cl.
  *G06Q 20/40* (2012.01)
  *A61B 3/14* (2006.01)
  *A61B 5/00* (2006.01)
  *G06Q 20/38* (2012.01)
  *G07C 9/00* (2006.01)

(52) U.S. Cl.
  CPC ..... *G06Q 20/40145* (2013.01); *G06Q 20/382* (2013.01); *G07C 9/00158* (2013.01)

(58) Field of Classification Search
  USPC ....................................................... 382/115
  See application file for complete search history.

(56) References Cited

U.S. PATENT DOCUMENTS

| 8,515,124 | B2 | 8/2013 | Yoo et al. |
| 8,591,030 | B2 | 11/2013 | Grecu et al. |
| 8,768,014 | B2 | 7/2014 | Du et al. |
| 9,245,173 | B2 | 1/2016 | Lee et al. |
| 2008/0252849 | A1 | 10/2008 | Van Saarloos |
| 2008/0304011 | A1 | 12/2008 | Ng et al. |
| 2012/0293773 | A1* | 11/2012 | Publicover ............ A61B 3/113 351/210 |
| 2014/0337930 | A1* | 11/2014 | Hoyos ................... H04L 63/10 726/4 |
| 2015/0029461 | A1* | 1/2015 | Hoshino ............... A61B 3/113 351/206 |
| 2015/0294464 | A1 | 10/2015 | Kim et al. |

FOREIGN PATENT DOCUMENTS

| KR | 1020070094112 A | 9/2007 | |
| KR | 101159164 B1 | 6/2012 | |
| KR | 1020120127560 A | 11/2012 | |
| KR | 101286454 B1 | 7/2013 | |
| KR | 101417415 B1 | 7/2014 | |
| WO | WO-2014151114 A1 * | 9/2014 | ........... A61B 3/0008 |

OTHER PUBLICATIONS

People "Video Magnification" (4 pages total), http://people.csail.mit.edu/nirub/yktniag/, Jun. 2015.
EyeVerify "EyeVerify is making a few changes" (3 pages total), https://www.eyev eri fy. com/, 2017.

* cited by examiner

Sclera Vein Patterns

FIG. 18A
FIG. 18B
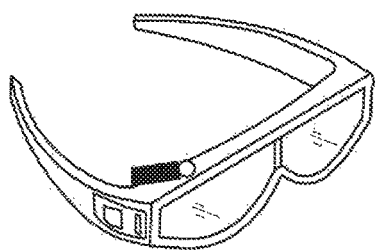
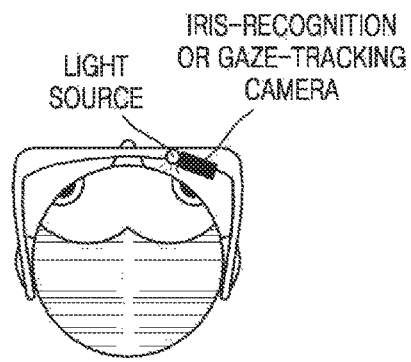
FIG. 18C
FIG. 18D
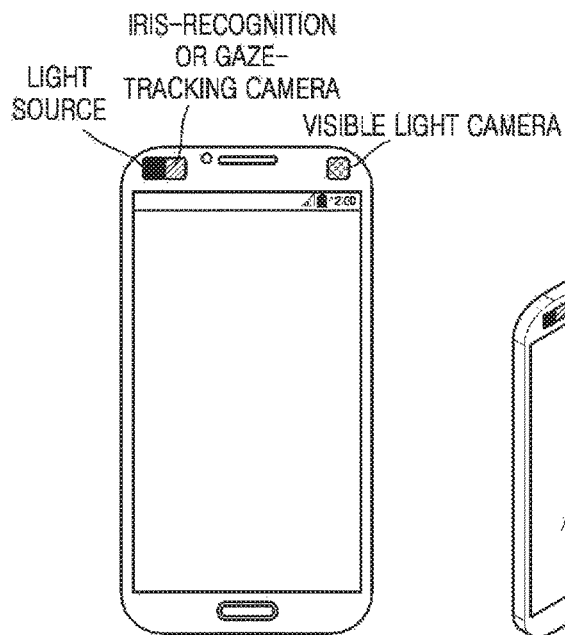
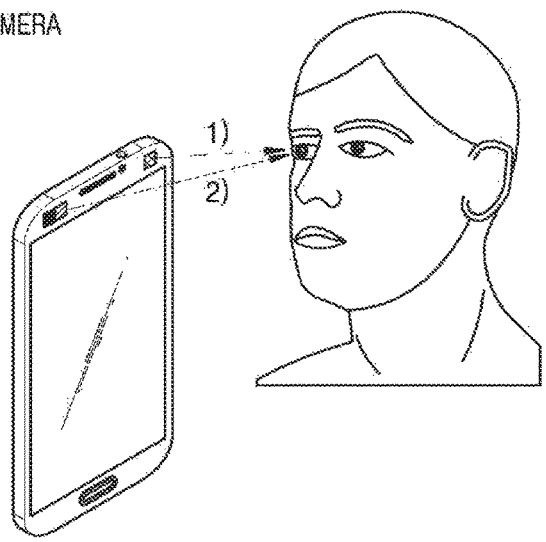

BIOMETRIC INFORMATION ACQUISITION METHOD AND DEVICE FOR SAME

CROSS-REFERENCE TO RELATED APPLICATIONS

This application is a National stage entry of International Application No. PCT/KR2016/002193, filed on Mar. 4, 2016, which claims priority from Korean Patent Application No. 10-2015-0043296, filed on Mar. 27, 2015 in the Korean Intellectual Property Office. The disclosures of each of the applications are herein incorporated by reference in their entirety.

TECHNICAL FIELD

The present disclosure relates to a method of acquiring biometric information, and more particularly, to a method of measuring a pulse using eyeball images.

BACKGROUND ART

With the development of information and communications technology, a variety of security systems are required. Financial transaction systems of banks require a customer's identification information, and fields of development of new technologies, such as research laboratories, also require improved security. Recently, due to these demands for improved security, various security technologies are being developed. As unique identification information of a user, various information for identifying the user, such as the user's voice, handwriting, etc., as well as a password arbitrarily set by the user is being used.

Lately, iris information is being used as identification information of a user, and security technology employing iris information is being developed. Because an iris is a physical feature of an individual user and causes no worry about loss or forgetting, iris authentication technology is attracting attention in terms of convenience. However, when an iris is artificially copied, a loss of usefulness as unique information of a user may be a problem.

Therefore, to compensate for existing user authentication technology employing an iris, there is an increasing need to use information on a sclera region around an iris as meaningful information. In particular, a sclera region has a brighter color than an iris, and changes in its color and brightness may be easily detected. Therefore, it is possible to detect a change of blood flow in a sclera, and a method of acquiring biometric information, such as a pulse, etc., through information on the change is proposed.

DETAILED DESCRIPTION OF THE INVENTION

Technical Problem

Provided is a method of acquiring biometric information using information included in a sclera region of an ocular region.

Additional aspects will be set forth in part in the description which follows and, in part, will be apparent from the description, or may be learned by practice of the presented exemplary embodiments.

According to an aspect of an exemplary embodiment, a method for a device to acquire biometric information includes acquiring a plurality of images including an ocular region using an infrared ray (IR) image sensor, detecting a sclera region in each of the plurality of acquired images, sensing a change of the detected sclera region, and determining biometric information based on information on the sensed change of the sclera region.

Technical Solution

According to an aspect of an exemplary embodiment, a method for a device to acquire biometric information includes acquiring a plurality of images including an ocular region using an infrared ray (IR) image sensor, detecting a sclera region in each of the plurality of acquired images, sensing a change of the detected sclera region, and determining biometric information based on information on the sensed change of the sclera region.

DESCRIPTION OF THE DRAWINGS

These and/or other aspects will become apparent and more readily appreciated from the following description of the exemplary embodiments, taken in conjunction with the accompanying drawings in which:

FIGS. 18A to 18D show devices including an image acquisition unit according to an embodiment of the present disclosure;

BEST MODE

Figure 1A:
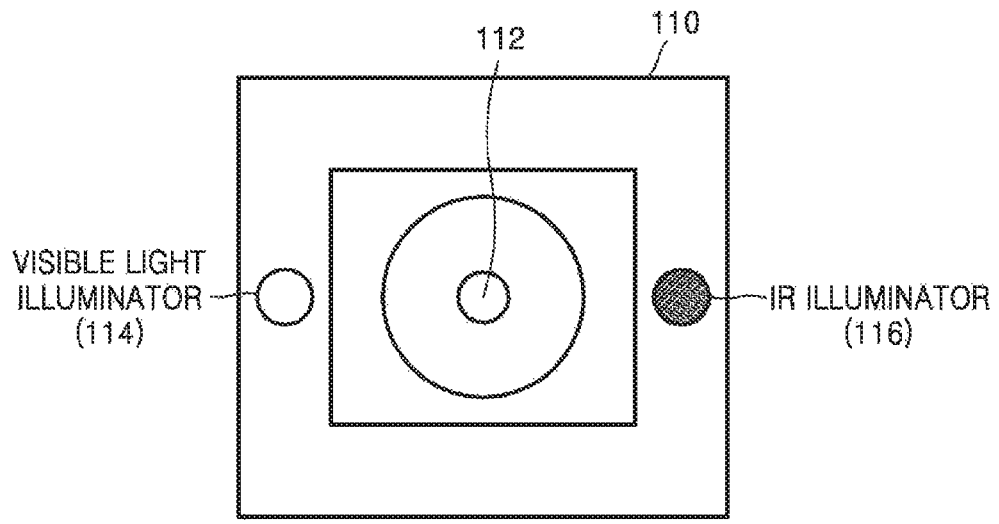
FIGS. 1A to 1C show a light source and an imaging module according to an embodiment of the present disclosure.

According to an aspect of an exemplary embodiment, a method for a device to acquire biometric information includes acquiring a plurality of images including an ocular region using an infrared ray (IR) image sensor, detecting a sclera region in each of the plurality of acquired images, sensing a change of the detected sclera region, and determining biometric information based on information on the sensed change of the sclera region.

The biometric information may include at least one of pulse information and distribution information of capillary vessels.

The change of the sclera region may include at least one of a color change and a brightness change of the sclera region.

The brightness change of the sclera region may be caused by contraction and expansion of capillary vessels in the sclera region.

The contraction and expansion of the capillary vessels in the sclera region may be changes repeated at regular time intervals.

The detecting of the sclera region may include detecting the ocular region in the images including the ocular region, and detecting the sclera region in the detected ocular region.

The method may further include detecting an iris region in the acquired images including the ocular region.

The method may further include identifying a user based on a pattern of the detected iris region.

The determining of the biometric information based on the information on the sensed change of the sclera region may include binarizing the information on the sensed change of the sclera region.

According to another aspect of another exemplary embodiment, a device for acquiring biometric information includes an image acquisition unit configured to acquire a plurality of images including an ocular region using an IR image sensor, a storage configured to store the plurality of acquired images, and a controller, wherein the controller includes a sclera detector configured to detect a sclera region in the plurality of acquired images, and is set to sense a change of images of the detected sclera region and determine biometric information based on information on the sensed change of the detected sclera region.

Mode of the Invention

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

These embodiments relate to a method and device for acquiring biometric information, and description of details widely known to those of ordinary skill in the art to which the following embodiments pertain will be omitted.

FIGS. 1A to aC show a light source and an imaging module according to an embodiment of the present disclosure.

As a method of acquiring biometric information of a user or a method of authenticating a user, methods employing unique information of an ocular region of a user are being developed. Because each user has a unique iris pattern, fields in which an iris pattern is analyzed to measure biometric information of a user or to be used as authentication information are attracting attention.

To analyze iris information of a user, information on an image captured using an eyeball of the user as a subject is necessary, and a device may detect an image of such an ocular region in an image of the user.

Figure 1B:
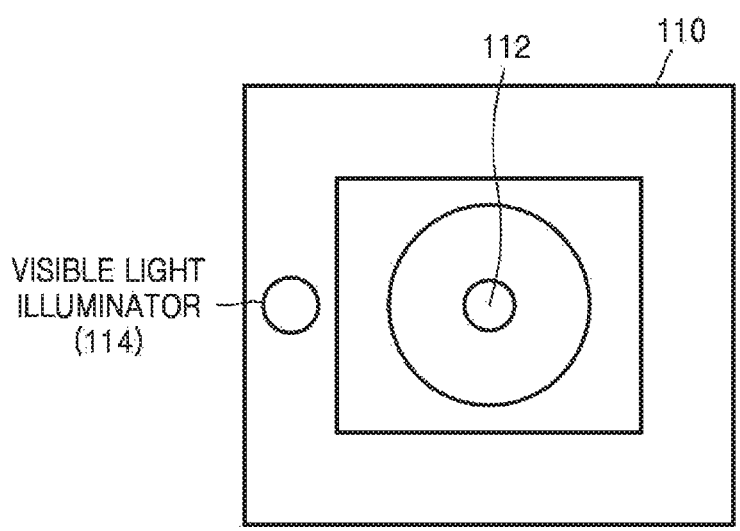
Figure 1C:
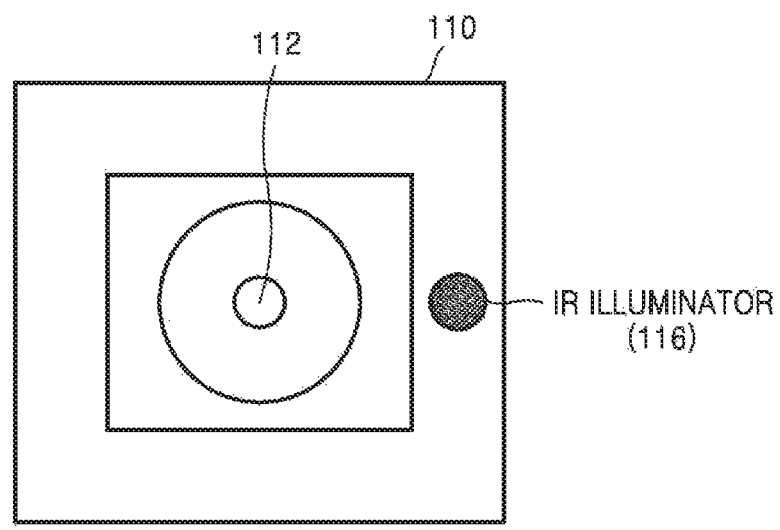

As shown in FIGS. 1A to 1C, the device may include an image acquisition unit 110. In embodiments of the present disclosure, an image may be a moving image captured during a certain time as well as an image of a certain moment.

In general, the image acquisition unit 110, such as a camera, acquires light which is emitted from a visible light source and reflected by a subject. Because a general image acquisition process is well-known technology, detailed description thereof will be omitted.

In addition to a lens 112, the image acquisition unit 110 may include an illuminator. As shown in FIG. 1A, the illuminator may include both a visible light illuminator 114 and an IR illuminator 116. The image acquisition unit 110 acquires light of a visible light illuminator reflected by the subject, and thus may include only the visible light illuminator 114 as shown in FIG. 1B in consideration of portability or cost. Instead of the visible light illuminator 114, the image acquisition unit 110 may include only the IR illuminator 116 as shown in FIG. 1C.

It is possible to determine whether to use the visible light illuminator 114 or the IR illuminator 116 as the illuminator according to features, the size, etc. of a subject.

The IR illuminator 116 may be used in the image acquisition unit 110 for the following reason. An iris region has a doughnut shape composed of a pupil boundary (inner edge of a pupil) and an iris boundary (outer edge of an iris). In a brown eye under visible light illumination, brightness of the iris and brightness of the pupil are similar to each other, and it may be difficult to see the pupil boundary. However, under IR illumination or in a black-and-white camera environment, since there is a large brightness difference between the iris and the pupil, the iris region having the doughnut shape may be clearly revealed. Therefore, it may be efficient to use the IR illuminator 116 for detecting the iris region.

A method of acquiring biometric information of a user by analyzing an image captured by the image acquisition unit 110 including the visible light illuminator 114 and/or the IR illuminator 116 will be described below.

Figure 2:
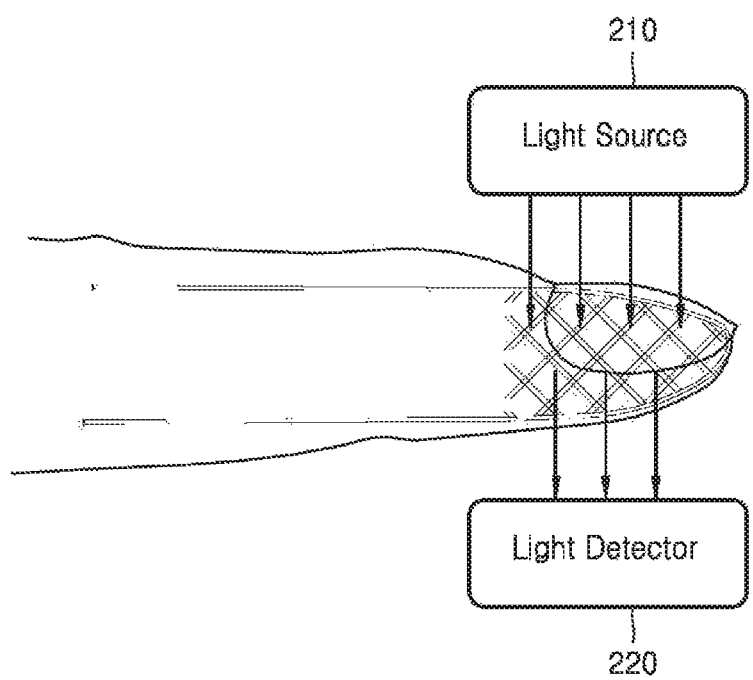
FIG. 2 illustrates photoplethysmography (PPG) according to an embodiment of the present disclosure.

FIG. 2 illustrates photoplethysmography (PPG) according to an embodiment of the present disclosure.

The device may acquire pulse information of a user as biometric information of the user. As a method of acquiring pulse information of a user, PPG may be used. Hemoglobin (Hb) included in blood is characterized by absorbing light, and may affect the amount of light reflected and transmitted according to an expansion and a contraction of blood vessels dependent on the user's pulse. Therefore, a technology applying such a feature to a pulse sensing or an oxygen saturation measurement is referred to as PPG.

PPG is a pulse wave estimation method of estimating a heartbeat state by measuring the amount of blood flowing through a blood vessel using optical features of biological tissue. A pulse wave is a pulsating waveform shown when blood is pumped wavelike from a heart, and may be measured through a change of blood flow caused by an expansion and a contraction of the heart and a resultant change of the volume of a blood vessel. PPG employs a photoplethysmogram for observing optical features, such as a light reflectance, absorbance, transmittance, etc., of biological tissue shown when the volume of a blood vessel changes, and a heartbeat is measured through the change.

PPG may be classified as transmissive PPG and reflective PPG according to locations of a light source 210 which emits light and a light detector 220 which senses the light.

As shown in FIG. 2, a method in which the light source 210 and the light detector 220 are located opposite to each other with skin tissue interposed therebetween and the light detector 220 senses transmitted light rays among incident light rays is a method limited to use on end portions of a body without non-transmissive tissue, such as bones.

A light source used in PPG may differ according to its usage. A green light-emitting diode (LED) may be used for heartbeat measurement, and a red LED may be used for oxygen saturation measurement.

A transmissive PPG sensor is a generally used PPG method, and has a form attached to a fingertip or so on. The transmissive PPG sensor has drawbacks in that a light signal received by a light detector is strong, it is more affected by noise than a reflective PPG sensor due to a longer travel distance of light, and it is relatively possible to use it only for end portions of a body without non-transmissive tissue, such as bones.

Figure 3A:
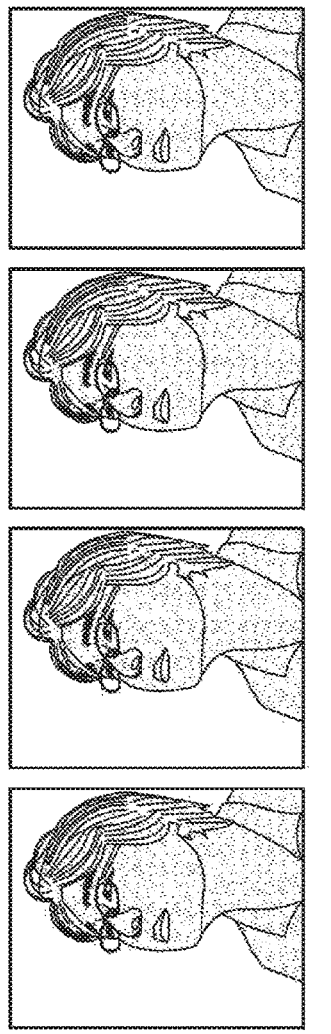
FIGS. 3A to 3C show an example in which PPG is applied according to an embodiment of the present disclosure.
Figure 3B:
Figure 3C:
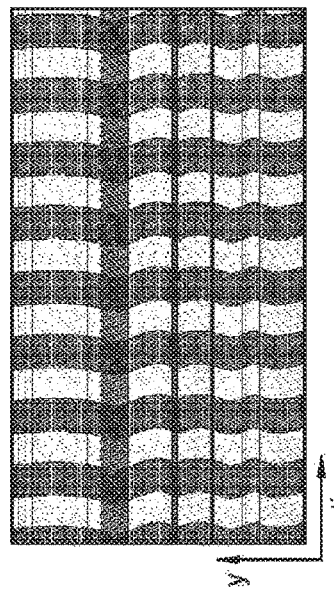

FIGS. 3A to 3C show an example in which PPG employing visible light is applied according to an embodiment of the present disclosure.

As shown in FIGS. 3A to 3C, it is possible to perform optical blood flow measurement by sensing reflected light of a light source of the device. In comparison with the transmissive optical blood flow measurement of FIG. 2, this is less limited in terms of applicable physical portions. Also, visible light is used, and thus it is convenient that an illuminator, such as an IR illuminator, is not additionally necessary.

A controller of the device may analyze information on a change in a plurality of acquired images. The controller of the device may analyze information on a change of color, brightness, and movement over time in the plurality of images.

The controller of the device may magnify a spatiotemporal change in the plurality of images through color enhancement. FIG. 3A shows consecutively acquired images. Consecutive acquisition of images denotes images which are acquired within a certain time according to a setting or input of a user. The plurality of images may have the same time intervals or different time intervals, but the former is better. In the acquired images of FIG. 3A, a color change of a person's face is repeatedly sensed, and may be magnified to measure a frequency signal of the repeated change.

The upper diagram of FIG. 3C represents average color values y of vertical lines versus time in FIG. 3A, and the lower diagram of FIG. 3C represents average color values of vertical lines versus time in FIG. 3B. According to whether or not a changed color magnification operation has been performed, the upper and lower diagrams of FIG. 3C show changes of the average color value over time.

Referring to time intervals at which the plurality of images are acquired, biometric information such as a pulse is acquired using an image sensor according to an embodiment of the present disclosure. Because the normal value of an adult's pulse is about 50 to about 100 beats per minute, it is necessary to acquire a larger number of images than a pulse rate per minute.

A plurality of images according to an embodiment of the present disclosure may be acquired about 240 or more times per minute. Through the images acquired at an image capturing speed of about 240 times per minute (about 4 times per second) or higher, the pattern of a pulse may be extracted, and using time interval information between a peak value and the next peak value, pulse information may be quantitatively determined.

A plurality of images according to another embodiment of the present disclosure may be acquired about 30 or more times per second. A large number of images may be necessary not just to determine a pulse rate but also to be used as biometric information for analyzing a precise pattern of a pulse and diagnosing arrhythmia or so on.

It is to be noted that the above description of time intervals between images is presented not to limit the present disclosure thereto but to illustrate appropriate time intervals between images for measuring various biometric information. Therefore, it is to be appreciated that the controller according to an embodiment of the present disclosure may determine biometric information using more or fewer images than those acquired at the aforementioned time intervals.

The plurality of images may be acquired under illumination of the visible light region rather than the IR region, or using both a visible light illuminator and an IR illuminator. A reference for selecting an illuminator has been described above with reference to FIG. 1, and the detailed description will not be reiterated.

The controller of the device may arrange a plurality of images whose change has been magnified through color enhancement based on the time axis, thereby analyzing spatiotemporal change information of the images. Light reflected on a person's face is changed in color, etc. by a blood flow of the person, and thus images may be changed at regular intervals like his or her pulse. The controller of the device may obtain the period by calculating a time between a peak value and the next peak value according to periodic change information of the images over time, and may acquire pulse information based on the obtained period.

Figure 4:
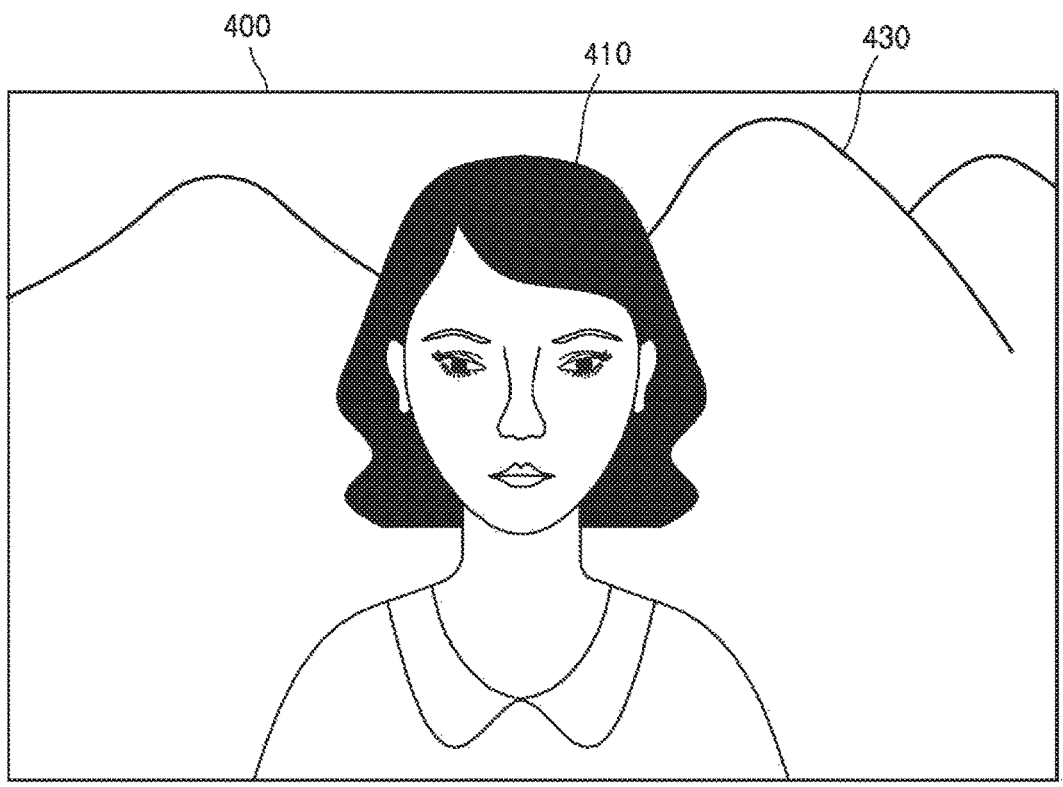
FIGS. 4 to 6 illustrate a method of detecting an ocular region according to an embodiment of the present disclosure.
Figure 5:
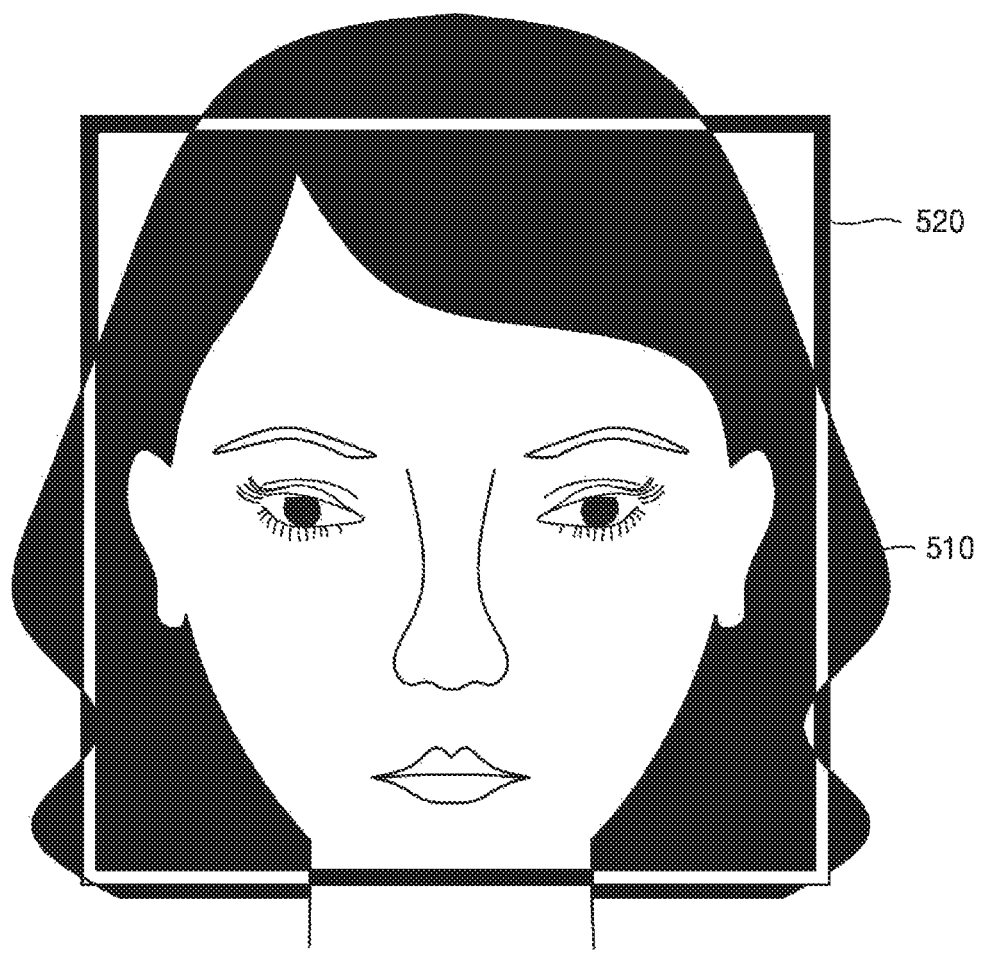
Figure 6:
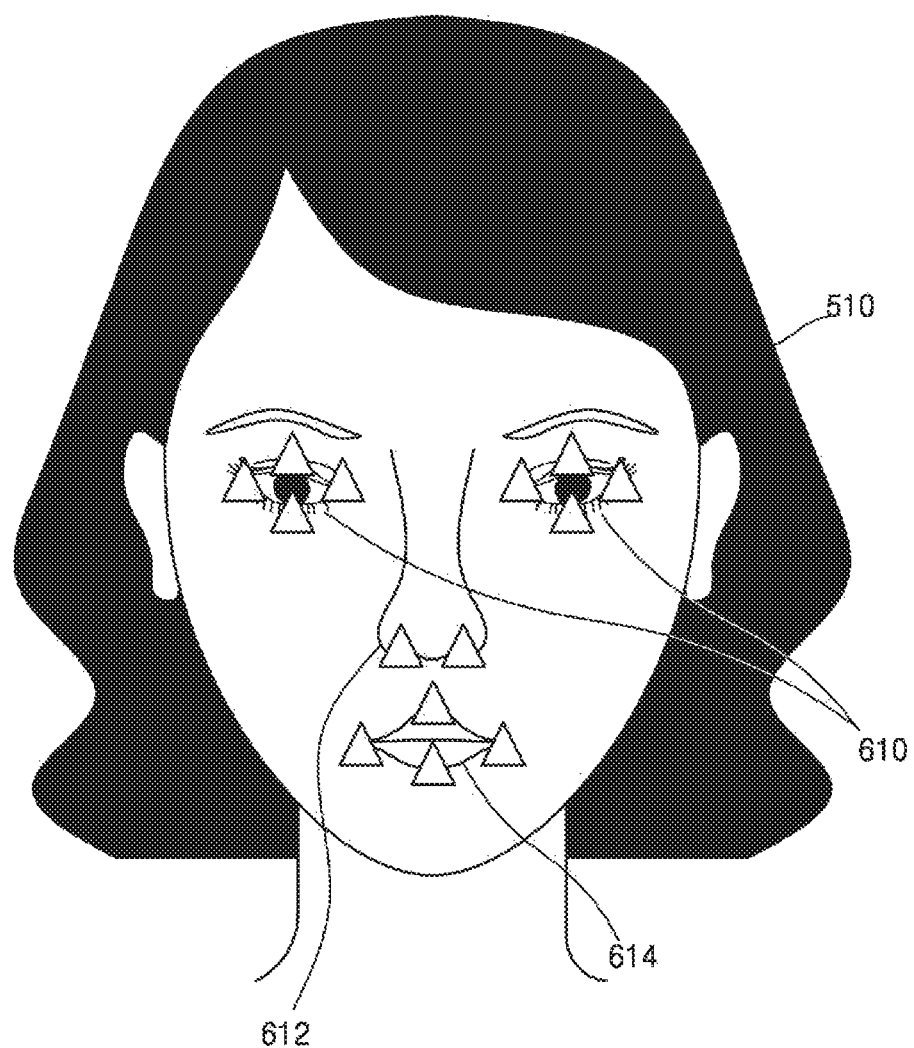

FIGS. 4 to 6 illustrate a method of detecting an ocular region in an image according to an embodiment of the present disclosure.

The image acquisition unit may receive a captured image. The captured image is a digital signal, but is not limited thereto. It is to be appreciated that the captured image is a wide concept including an analog signal.

The acquired image may be expressed in the three primary colors of the red-green-blue (RGB) color system. However, the acquired image is not limited to the RGB color system, and may be expressed in three primary colors of the hue-saturation-value (HSV) color system or the luminance-chrominance (YUV) color system, or colors of the cyan-magenta-yellow-black (CMYK) color system.

As shown in FIG. 4, the image acquisition unit of the device may acquire an image including a facial region of a person. As described above, it is possible to acquire a user's facial image by visible light reflected on the user's face or a user's facial image by infrared rays of an IR illuminator reflected on the user's face. Here, the acquired image may be a plurality of images or a moving image, and two or more images acquired at different times are sufficient.

An image 400 acquired by the image acquisition unit may include not only a cranial region 410 including a face of a person but also a background 430 distinguished from the person. In this case, it is necessary to distinguish between the person who is a subject and the background 430. In other words, it is necessary to distinguish the cranial region 410 of the person from the person. Alternatively, it is also possible to directly distinguish an ocular region of the user without a process of distinguishing the cranial region from the person who is a subject.

A cranial region may be distinguished in an acquired image by determining a similarity to an image previously stored in a database (DB) or using focus information, etc. in the acquired image. Because a cranial region is distinguished using existing methods, detailed description of a method of distinguishing a cranial region will be omitted.

As shown in FIGS. 5 and 6, the controller of the device may detect a facial region 520 of a user in an acquired image. In general, the detected facial region 520 shows a significant image difference according to the angle, rotation, and size of the face when the image acquisition unit acquires the image. The image difference may sensitively show the influence of a latitudinal change with respect to the background upon acquisition of the image.

As a method of detecting a facial region, a knowledge-based method, a feature-based method, a template-matching method, an appearance-based method, etc. may be used.

According to the knowledge-based method, a face is detected using the fact that a person's face includes two symmetrical eyes, one nose, and one mouth, and the elements have fixed distances and location relationships therebetween. Using this method, it is difficult to detect a face in images in which the face shows various changes, such as a slope of the face, an angle at which the person looks at a camera, illumination, a facial expression, etc., and thus it is possible to use this method only in an ideal case.

According to the feature-based method, unchangeable features of a face, such as a skin color, texture, the size of component features, a shape, etc., are used. In particular, facial detection using the skin color may be used irrespective of rotation, a posture, the size, etc. of the face, and thus has a short processing time. However, with a background or entity having a color similar to a skin color, the component features of the face may not be detected. Also, due to illumination, the skin color may be distorted, or the texture may be lost. To solve these problems, an algorithm in which various facial elements are integrated is being researched.

According to the template-matching method, a standard template is generated for a facial form, ocular regions 610, a noise 612, a mouth 614, etc. and then compared with an input image to measure feature correlation and detect a face. This method is less sensitive to an illumination change or the influence of a background, and enables facial detection in a complex background. However, according to this method, it is difficult to cope with a change of a face size according to distance and changes according to rotation, an image acquisition angle, etc., and it is also difficult to generate an average template including all information of all people.

According to the appearance-based method, features that clearly represent a difference between a face image and a background image are found to generate and learn a learning data set of complex images, and then a face is detected using learned models.

Using a suitable one of the above methods, the controller of the device may detect a facial region of a user. In the present disclosure, the above four methods are described as facial detection methods, but a facial detection method is not limited thereto. Using a method used in this field among unmentioned methods, it is possible to detect a facial region.

The controller of the device may detect the ocular regions 610 in the detected facial region. In the same method as or a similar method to the facial region detection method, ocular regions may be detected. The ocular regions 610 are regions including two eyes, and a concept including regions close to the two eyes (irises).

The controller of the device may directly detect ocular regions without the operation of detecting a facial region in an image. The operation in which the controller detects a facial region is not a necessary operation, and may be appreciated as a process that is additionally performed to more accurately detect ocular regions.

Irises of the two eyes may have a color close to black compared to surrounding regions, and due to such a color difference, it is possible to detect ocular regions. Based on existing iris recognition technology, numerous iris region detection methods have been developed. The iris region detection method of the present disclosure is not limited to a certain method, and it is possible to use any method in which the iris region may be distinguished from a surrounding region.

A method of acquiring biometric information using a sclera region in an ocular region proposed in the present disclosure will be described below.

FIGS. 7A, 7B, 8A, and 8B show a structure of an eye according to an embodiment of the present disclosure.

Figure 7A:
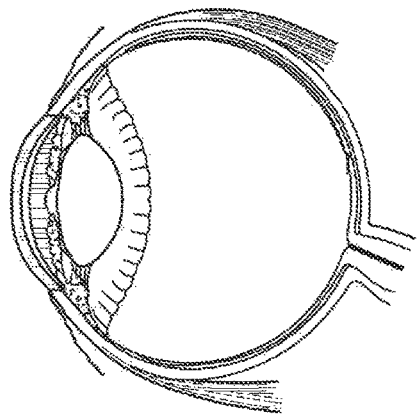
FIGS. 7A, 7B, 8A, and 8B show a structure of an eye according to an embodiment of the present disclosure.
Figure 8A:
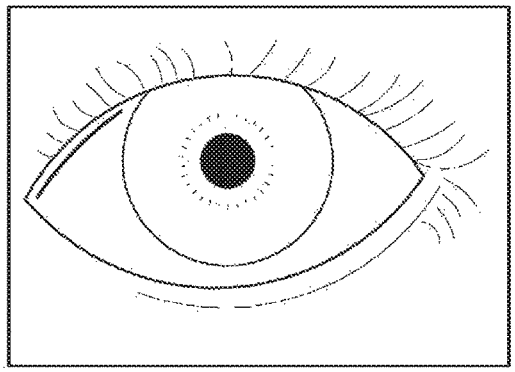
Figure 8B:
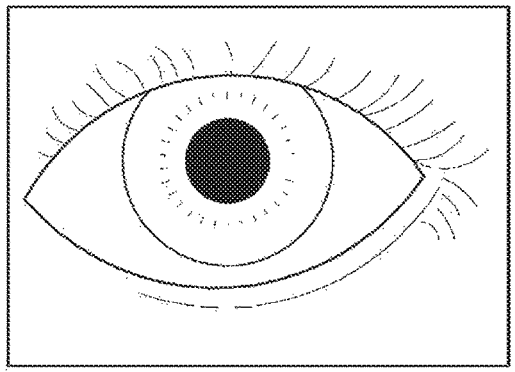

As shown in FIG. 7A, an eyeball includes various parts, and roles in image acquisition are distributed to the respective parts. An iris serves to adjust the amount of light incident on the eye. As shown in FIG. 8A, in a bright environment, the iris expands to reduce the pupil, thereby preventing a large amount of light from entering. On the other hand, as shown in FIG. 8B, in a dark environment, the iris contracts to dilate the pupil, thereby causing the pupil to receive light. According to brightness, the pupil boundary changes, but the iris boundary does not significantly change. The sclera is the outermost layer of the eyeball, and has a hard structure to maintain the shape of the eyeball. The sclera indicates a white region excluding the pupil. Although there are various other parts, detailed description thereof will be omitted in the present disclosure.

Figure 7B:
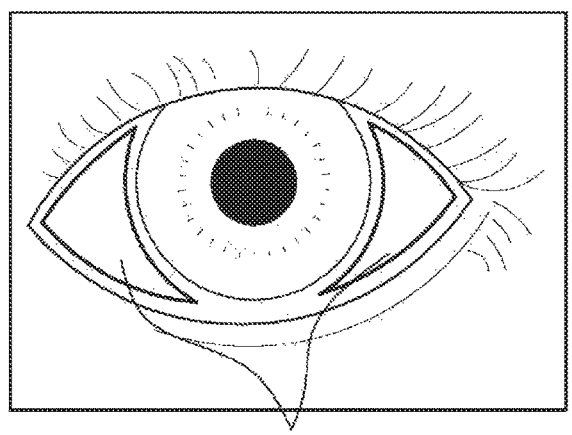

As shown in FIG. 7B, a portion of the eyeball outside the iris corresponds to a sclera region 70. During photography with an image acquisition unit, such as a camera, only a portion of the sclera region 70 excluding the iris region is exposed. However, the exposed portion is not always the same and may vary.

Figure 9:
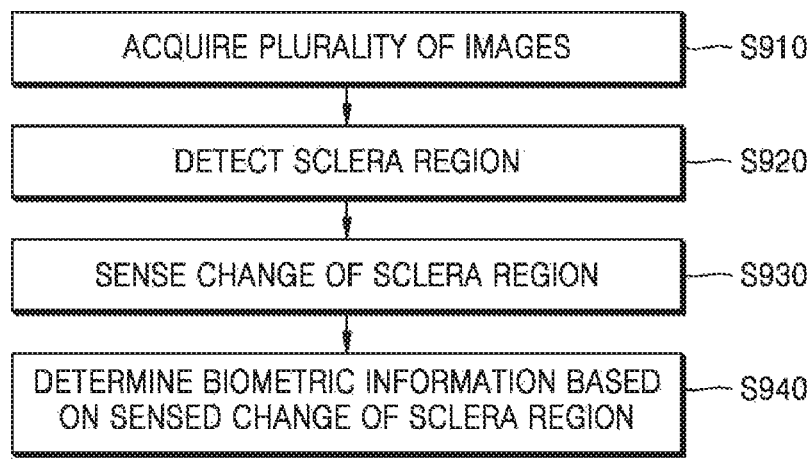
FIG. 9 is a flowchart illustrating a method of acquiring biometric information according to an embodiment of the present disclosure.

FIG. 9 is a flowchart illustrating a method of acquiring biometric information according to an embodiment of the present disclosure.

In operation S910, the device may acquire a plurality of images through the image acquisition unit. The acquired images may be images captured at certain moments or moving images captured for a certain time. Although embodiments of the present disclosure are described based on the assumption that the device includes the image acquisition unit, the image acquisition unit may be a separate device present outside the device. By receiving images captured by the image acquisition unit outside the device through a wired or wireless communication network, the device may acquire the images.

The acquired images may be images of a user's ocular region. Alternatively, the acquired images may be images in which the ocular region may be detected through enlargement or an image analysis.

To acquire a plurality of images, the image acquisition unit may capture an image at regular time intervals. For example, in the case of a human heartbeat, a normal value of adults is about 50 to about 100 beats per minute, and images may be acquired at an acquisition speed of about 240 times or more per minute which is higher than the normal value. Alternatively, a plurality of images may be captured at preset intervals. In another example, it is possible to capture an image about 30 times per second.

In this case, the image acquisition unit acquiring a plurality of images may be an IR image sensor. In the case of extracting an image of the sclera region through the IR image sensor, a reflected IR image may be captured without the influence of a change of visible light. While a visible light image sensor shows a significant change of light and shade according to day and night, an IR image is not significantly affected by such an influence.

When there is no IR image sensor, a plurality of images may be acquired using a visible image sensor. An IR image sensor may emit a wavelength including heat, and when an eyeball image is captured with a device, such as smart glasses, there is a danger that eyeballs may be heated. Therefore, an eyeball image may be acquired with a visible light image sensor.

In addition, an IR image sensor and a visible light image sensor may acquire images together, and use of an image sensor capable of accurately capturing an eyeball image according to circumstances is sufficient.

In operation S920, the controller may detect a sclera region in the acquired images. In the detected ocular region, a region excluding the iris region corresponds to the sclera region, and it is possible to detect the sclera region using various existing iris region detection methods.

In operation S930, the controller may sense an image change in the sclera region of the acquired images. An image change of the sclera region may be sensed based on a plurality of images. In the plurality of images acquired by the image acquisition unit, a change of the sclera region may be sensed at regular time intervals or according to a time set by the user. The controller may detect respective sclera region images in the plurality of acquired images and compare color and brightness information of the respective detected sclera region images, thereby sensing a change. In this case, information on the sensed change of the sclera region may be various information which changes over time, such as color information of the sclera region, brightness information of the sclera region, pattern information of capillary vessels in the sclera region, and so on.

As a method of sensing a change in a user's body, PPG may be used. A PPG signal is a signal for measuring changes of the amounts of absorption, reflection, and dispersion of light radiated to blood in a blood vessel which changes according to a heartbeat, and reflects a syndrome related to peripheral blood vessels. In the field of medical measurement, the PPG signal is analyzed to measure a pulse and a blood oxygen saturation level in a stable state.

When an oxygen level is lowered, fatigue materials increase in a user's body or a physical activity level is lowered, such as a lack of concentration or so on. Therefore, the device may measure an oxygen saturation level and perform various environmental improvement actions, such as a recommendation for a deep breath, ventilation of air, and so on. In general, a green LED light source may be used for measuring a heartbeat, and a red LED light source may be used for measuring an oxygen saturation level.

To measure an oxygen saturation level, two or more reactions having different wavelengths are necessary, and thus additional equipment may be necessary. In this case, the device may measure an oxygen saturation level in connection with the additional equipment by wire or wirelessly.

According to existing methods, a photoplethysmogram is frequently measured at a user's finger or earlobe in which many capillary vessels are present. According to general PPG, light emitted from an LED is reflected by or transmitted through skin, and then a change of the amount of light is measured using a light-receiving diode or a transistor.

Using a difference between PPG signal peak values elicited by a PPG measurement circuit, it is possible to continuously measure a pulse, a blood pressure, and so on. Based on the basic principle of such PPG, by radiating uniform light from a light source, such as an LED, etc., to a sclera region of an eyeball in which capillary vessels are present and acquiring a reflected image with a camera, it is possible to measure a user's pulse, change in blood flow change, oxygen saturation level, and so on.

The controller may sense a change of the color of the sclera region in the acquired images. In the plurality of images received from the image acquisition unit, it is possible to detect a change of the color of the sclera region over time. Among the plurality of images, the color of the sclera region in a first image and the color of the sclera region in a second image may differ from each other. Since the blood flow of capillary vessels present in the sclera region is changed by a heartbeat, the color of the sclera region may also be changed.

The controller may sense a change of the brightness of the sclera region in the acquired images. As with a color change of the sclera region, the blood flow of capillary vessels present in the sclera region is changed by a heartbeat, and thus the brightness of light reflected at the sclera region may also be changed.

The controller may sense a pattern change of capillary vessels in the sclera region from the acquired images. Capillary patterns acquired from respective images may differ from each other because the blood flow of capillary vessels is changed by a heartbeat. However, when a pattern itself is changed because each user has a unique capillary pattern, the controller may not sense a pattern change.

In operation S940, the controller may determine biometric information based on information of the sensed change of the sclera region. The controller may control a storage to store the change information of a color, brightness, a capillary vessel pattern, etc. of the sclera region.

The change information of the sclera region may be analyzed by information changed over time. By magnifying a feature color which is slightly changed over time, it is possible to further emphasize a difference between values changed over time.

Based on the values before and after the change, the controller may determine a pulse, a blood pressure, an oxygen saturation level, distribution information of capillary vessels, etc. of a user who is a subject. Because the user's pulse is a pulse based on a heartbeat, it is possible to determine the user's heart rate by determining the pulse. Also, the controller may determine the user's oxygen saturation level. An oxygen saturation level is information representing a ratio of oxygen actually bound to the oxygen-carrying capability of Hb in red blood cells within a human body as a percentage. Biometric information such as a blood pressure and an oxygen saturation level may demand additional equipment as well as the image acquisition unit according to an embodiment of the present disclosure. An electrocardiography (ECG) device may be necessary for blood pressure measurement, and a light source having two or more wavelengths may be necessary to measure an oxygen saturation level.

The controller may measure the blood pressure based on the change information of the acquired images of the sclera region. To measure the blood pressure, an additional ECG signal measuring device may be provided, and the blood pressure may also be simultaneously measured by a head mounted display (HMD) which is a head mounted tool having a camera for photographing an eyeball. While an ECG signal is an electrical signal propagating upon a heartbeat, a pulse wave measured at an eyeball by PPG is transferred by physical propagation of a blood pressure. Therefore, there is a time difference between peaks of the ECG signal and the pulse wave. It has been known that the propagation rate of a pulse wave through blood vessels varies according to the hardness of arteries. In general, as arteries are hardened and a casual blood pressure is higher, the propagation rate of the pulse wave through blood vessels increases, and the difference in transfer time between the ECG signal and the pulse wave measured by PPG decreases. Therefore, it is possible to relatively determine that the blood pressure is low when there is a large time difference between peaks of the ECG signal and the pulse wave measured at the eyeball, and the blood pressure is high when there is a small time difference.

In the sclera region, light of a first wavelength (e.g., about 660 nm) at which the absorption of reduced Hb is higher than the absorption of oxidized Hb and light of a second wavelength (e.g., about 940 nm) at which the absorption of oxidized Hb is higher than the absorption of reduced Hb are measured, and a ratio of the two wavelengths are used as a variable to calculate the oxygen saturation level.

The controller may notify the user of the determined biometric information or use the determined biometric information as monitoring information, authentication information, or so on. An example of the use will be described later.

A method of detecting a sclera region according to an embodiment of the present disclosure will be described in detail below.

Sclera Boundary Detection

Figure 10:
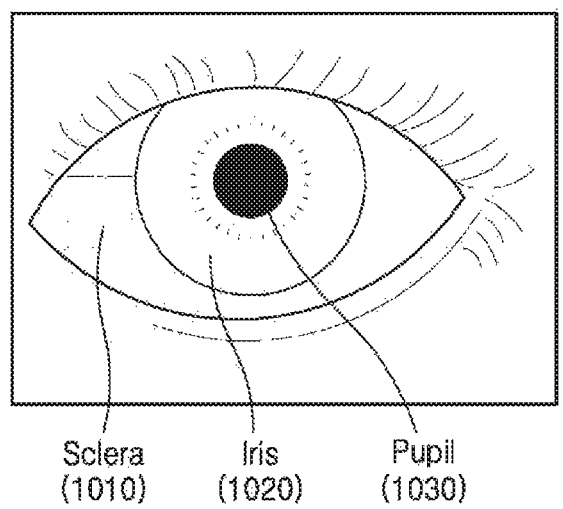
FIG. 10 shows a sclera region and an iris region according to an embodiment of the present disclosure.

FIG. 10 shows a sclera region and an iris region according to an embodiment of the present disclosure.

A human eyeball includes an iris region, and a region excluding an iris may be classified as a sclera region. At the center of the iris region, a circular pupil region is present, and the boundary between the pupil and the iris may be referred to as the pupil boundary as described above.

In the present disclosure, the sclera region in an ocular region is in focus, and thus a process of accurately detecting the sclera region is necessary. Therefore, it is necessary to accurately detect the boundary between the iris region and the sclera region.

As shown in FIG. 10, a pupil, an iris, and a sclera are respective regions constituting an eyeball. The controller of the device may accurately detect the sclera region by clearly distinguishing the respective regions from each other. When observed from the outside, the pupil has a circular shape in black. The pupil is black because light is absorbed into the eyeball through the pupil and there is almost no reflected light. Therefore, regardless of eye color, every pupil is black.

The iris serves to adjust the size of the pupil outside the pupil, and has a boundary with the sclera region. To detect the sclera region in an image, the controller of the device may use a method similar to that used to detect the iris region. This is because the whole region outside the iris boundary is regarded as the sclera region. Since the boundary between the sclera and the iris is the boundary between the sclera region which is relatively white and the iris region which is relatively black, it is possible to clearly detect the boundary through a color contrast process.

Various application examples of biometric information measurement based on a change of the sclera region according to embodiments of the present disclosure will be described below.

Pulse Measurement

As described above with reference to FIG. 9, the controller of the device may measure a user's pulse using change information of the user's sclera region images. When the change information of a sclera region is used, it is possible to measure the user's pulse in a contactless method rather than existing contact methods. Also, pulse measurement is performed without a particular device, so convenience of use may be improved.

The change information of a sclera region may correspond to various information which changes over time, such as color information of the sclera region, brightness information of the sclera region, pattern information of capillary vessels in the sclera region, and so on.

The color information or the brightness information of the sclera region may be determined by analyzing light that is emitted from a light source, such as a visible light illuminator or an IR illuminator, and reflected at the ocular region. Because the blood flow of capillary vessels in the sclera region may be changed over time by a heartbeat, it is possible to measure the pulse based on the change information.

To easily obtain change information according to time in a plurality of images, the device may magnify a color or brightness contrast between the images and make an analysis. In this case, the color and brightness of a sclera region image at a point in time of the largest amount of blood flow and those of a sclera region image at a point in time of the smallest amount of blood flow may differ from each other enough to be distinguishable from each other.

FIGS. 11 to 14 show a method of measuring a pulse according to an embodiment of the present disclosure.

Figure 11:
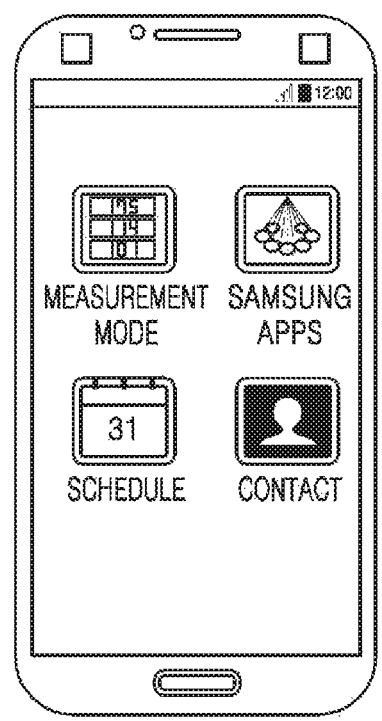
FIGS. 11 to 14 show a method of measuring a pulse according to an embodiment of the present disclosure.

An application for measuring a pulse may be installed in a smart phone, and the measurement application may be displayed on a display unit of the smart phone as shown in FIG. 11. The measurement application may measure a user's pulse, blood pressure, oxygen saturation level, arrhythmia, and so on.

Such a measurement application may be executed under various conditions. The measurement application may be executed by an execution command of the user, or may be automatically executed upon satisfaction of a preset condition. The preset condition may be a time intervals that is set by the user. For example, when the user sets the measurement application to be executed at 10 AM every day, the application may be executed at the time.

As another example of the preset condition according to an embodiment of the present disclosure, an execution command may be received through communication with an external device. An external device whose user is registered or which is permitted by the user transmits a command signal, and the command signal may be received to execute the measurement application. For example, when a hospital requesting measurement records of the user transmits a pulse measurement command to the corresponding device through a wired or wireless communication network, the device may execute a pulse measurement application and transmit the pulse measurement result information back to the hospital.

For the convenience of description, an example of a condition for executing a measurement application has been described. However, the present disclosure is not limited to the example, and a measurement application may be executed in a variety of ways or under a variety of conditions.

Figure 12:
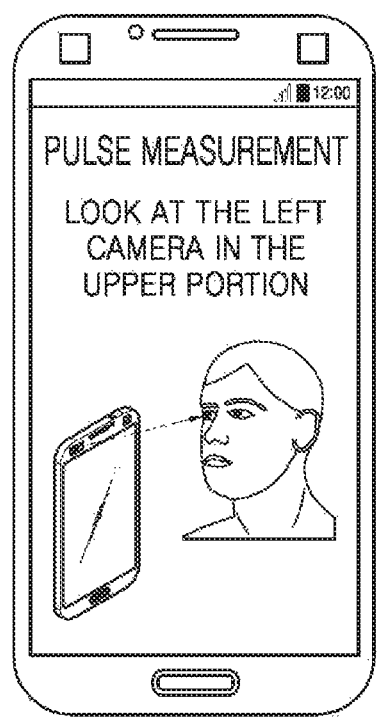

As shown in FIG. 12, the pulse measurement application may output measurement-related guide information to the user. Because pulse measurement is performed through a sclera of the user's eyeball, guide information may be displayed so that the user may look at a camera. For example, when an IR camera is disposed at an upperleft portion on the front side of the smart phone, the display unit may display text such as "Look at the left camera in the upper portion." Alternatively, measurement-related guide information may be output to the user through a blink of an LED lamp, acoustic information, a vibration, etc. in addition to text.

When it is not possible to acquire a sclera image of the user's eyeball, the smart phone may output guide information so that the user may appropriately move his or her eyes. For example, when the user is closing his or her eyes or blinks at a certain time interval or less, it is difficult to acquire an image of the user's sclera region, and thus the display unit may display text such as "Open your eyes and look at the left camera in the upper portion."

Figure 13:
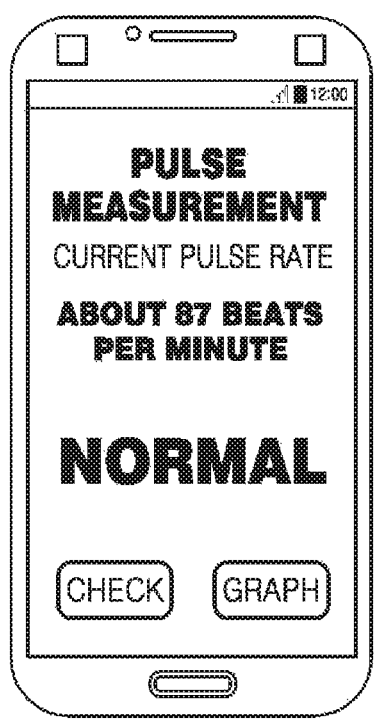

As shown in FIG. 13, a controller of the smart phone may determine pulse information by analyzing a plurality of images acquired by the camera. The controller may detect the sclera region in a plurality of images, and determine a pulse of the user who is the subject by analyzing brightness and color change information of images of the sclera region.

The display unit may display information on the determined pulse. As shown in FIG. 13, quantitative information "about 87 beats per minute" may be displayed, and qualitative information, such as "normal," "high pulse rate," or "low pulse rate," may also be displayed. Such a display method may be changed or fixed by the user or under a preset condition, and may be set to display only meaningful information.

The display unit may output pulse information in various ways including the method of displaying pulse information on a display. The smart phone according to an embodiment of the present disclosure may cause an LED lamp to blink in the same pattern as the pulse information determined as the user's pulse, or may be set to vibrate in the same pattern as the pulse information. Alternatively, the pulse information may be output as acoustic information in the same pattern. When the pulse information is output in various ways, the user may sense his or her pulse through the smart phone using various senses, so that convenience is improved.

Figure 14:
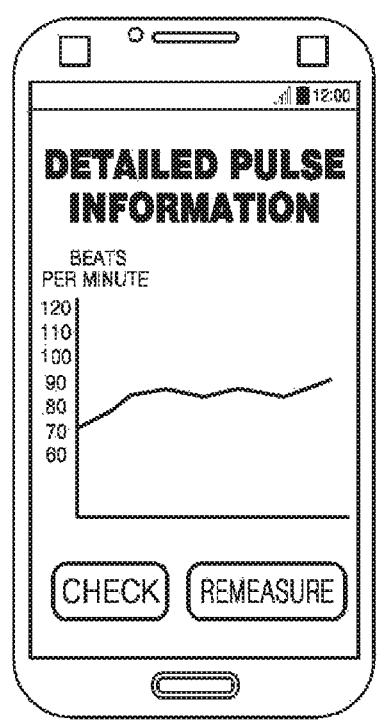

As shown in FIG. 14, the display unit may display the user's pulse pattern in detail in a graph. By receiving a command signal to display the pulse information in a graph from the user or under a predefined condition, the controller may display the pulse information in a graph. The display unit may display the pulse information obtained by analyzing the plurality of acquired images as information according to the flow of time. By displaying the pulse information in a graph, it is possible to provide an opportunity to check various biometric information, such as a case in which a pulse rate is different from a normal pulse rate, and so on.

Arrhythmia refers to a symptom in which the heart does not show a normal heart rate, that is, suddenly beats fast or slow or so on. The display unit may display the pulse information in a graph as shown in FIG. 14, thereby making it possible to check whether there is a symptom of arrhythmia. The controller of the smart phone may determine whether there is a change of a pulse pattern by comparing the user's pulse information stored in a storage and the current pulse information.

When it is determined that the information determined as the user's pulse information deviates from a normal value range, the controller of the smart phone may request the user to carry out the measurement again. For example, when the user's cumulative pulse information indicates a pulse rate of about 70 to about 100 beats per minute but it is determined that the current pulse information exceeds or does not reach a preset error range of the user's cumulative pulse information, the controller of the smart phone may request the user to carry out the measurement again.

When pulse information is measured again, the controller of the smart phone may acquire more images than those acquired for the previous measurement. For example, while images are generally acquired at a rate of four images per second for about 20 seconds to determine the user's pulse information, the controller may acquire images for remeasurement at a rate of 20 images per second for about 30 seconds to analyze precise pulse information.

The number of images per second is mentioned for the convenience of description, and the pulse measurement method of the present disclosure is not limited to the above conditions. The controller may determine a pulse rate with more or fewer images per second, and the camera may acquire images during a longer or shorter image acquisition time.

The controller of the smart phone may transmit the determined pulse information of the user to an external device. The pulse information of the user determined by the smart phone may be transmitted to a smart watch or other devices, such as the user's portable computer or smart glasses. For the transmission, a variety of wired and wireless communication methods, such as wireless fidelity (Wi-Fi), Bluetooth (BT), Zigbee, etc., may be used, and the pulse information may be transmitted regularly or irregularly.

The smart phone may communicate with a medical system connected to an external server. The medical system connected to the external server may be a system registered or permitted by the user. The smart phone may provide a remote medical treatment service to the user. The user's pulse may be measured by the smart phone which receives a manipulation or a command of a medical team, etc. from the external medical system, and pulse information may be transmitted back to the external medical system. At this time, the smart phone may transmit pulse history information of the user stored in the storage together.

Figure 15:
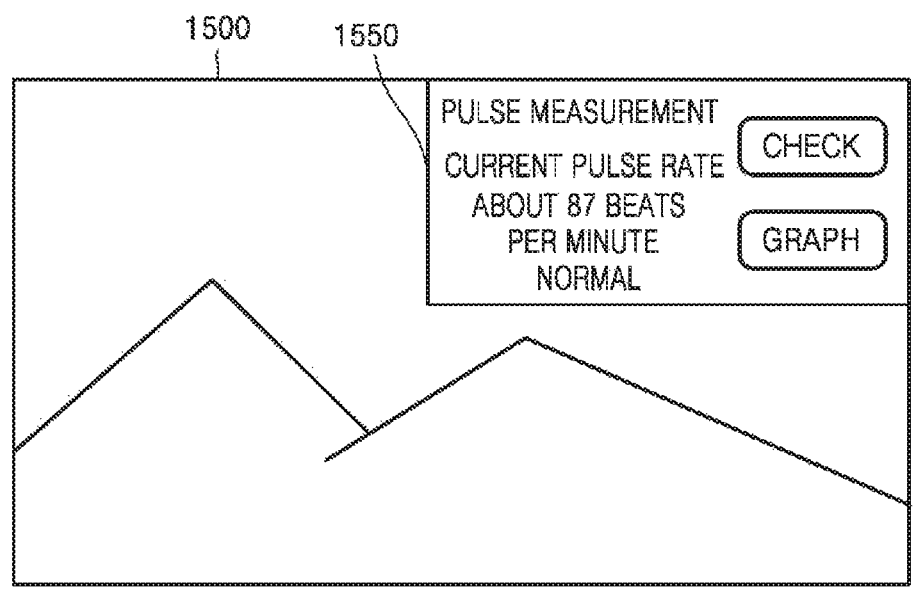
FIG. 15 shows a screen displayed in glasses according to an embodiment of the present disclosure.

FIG. 15 shows a screen displayed in smart glasses according to an embodiment of the present disclosure.

As shown in FIG. 15, a device according to an embodiment of the present disclosure may be a device of the same type as smart glasses. In the case of FIGS. 11 to 14, a device of the same type as a smart phone has been described above as an example. However, a device of the present disclosure is not limited thereto, and may be a device in various forms, such as a smart phone, a tablet PC, a computer, a glasses-type device, a band-type device, a watch-type device, a ring-type device, and so on. Any device having an image acquisition unit, such as a camera, may be the device described in the present disclosure.

The device according to the present disclosure may have the image acquisition unit and a controller as entities independent from each other. The image acquisition unit that acquires a plurality of images may be present as a separate device, and connected to a device including the controller by wire or wirelessly. When a sclera image of a user is acquired using an IR camera, the IR image acquisition unit may not be embedded in the device, and thus may be connected for use. Even in this case, the IR image acquisition unit may correspond to the device described in the present disclosure.

As shown in FIG. 15, there may be a screen 1500 that may be viewed by a user's eyes through glasses, and a display region 1550 in which information is displayed may be present in the glasses. In the display region 1550 in which information is displayed, the user's pulse information may be displayed. As described above with reference to FIGS. 11 to 14, a display unit may output measurement-related guide information to the user through a blink of an LED lamp, acoustic information, vibration, etc. in addition to text.

User Identification

The device may use biometric information of a sclera region as user identification information. Because every person has unique biometric information, it is possible to identify a person with a combination of unique biometric information.

The above-described pulse measurement method may be applied to user identification information. Because every person has unique pulse information, such as a pulse rate, a pulse pattern, etc., it may be possible to determine a person based on pulse information. However, people's pulses have similar average ranges, and thus may not be much used as identification information. Therefore, another identification method may be used.

Figure 16:
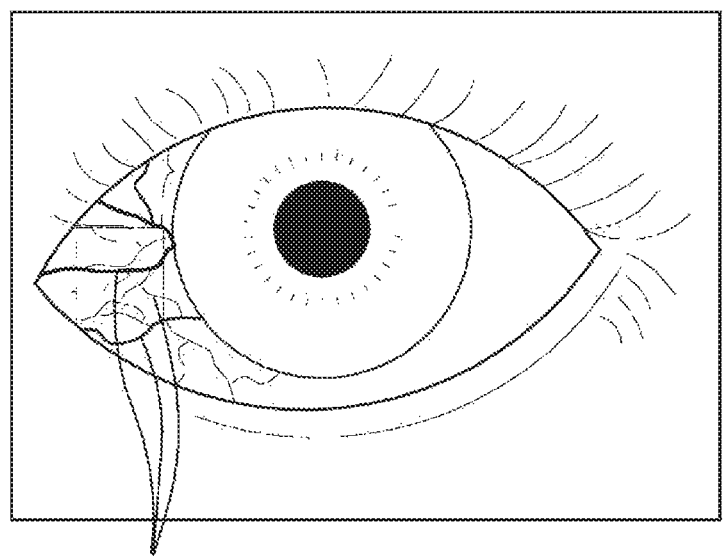
FIG. 16 shows capillary distribution in a sclera region according to an embodiment of the present disclosure.

FIG. 16 shows capillary vessels in a sclera region according to an embodiment of the present disclosure.

As shown in FIG. 16, there are capillary vessels in a user's sclera region, and a distribution pattern of the capillary vessels in the sclera region may be used as identification information. Therefore, pattern information of each user's capillary vessels may be stored in a DB, and it may be possible to identify a user with pattern information of capillary vessels in a sclera region of an image acquired thereafter.

As information for identifying a user, the controller may use pattern information of capillary vessels and the user's pulse information. Like a fingerprint, etc., capillary pattern information has a position as unique identification information. However, for more accurate identification, it may also be possible to identify a user using the user's cumulative pulse information together with the user's capillary pattern information. For example, a user's capillary pattern may be copied using a fake eyeball, etc., but the capillary pattern may be changed at the same intervals as a pulse. By comprehensively analyzing such a change, it is possible to identify the user.

When information of the sclera region is used as user identification information, different settings may be provided according to content for which the identification information is used. For example, the user authentication level of an application for financial transactions (account checking, money transfer, or stock transactions) may be set to be higher than that of an application for playing moving images. In another example, when pieces of content are electronic documents of the same type, a user authentication level may be set differently according to necessary security levels. As an example, the user authentication level of a document demanding security may be set to be higher than that of a document not demanding security. As another example, in the case of identical photograph files (or formats), the user authentication level of a photograph file demanding private protection may be set to be higher than that of a photograph file not demanding private protection.

In an embodiment, authentication levels for content may be stored in the form of a table in a memory. For example, authentication levels for content may be stored as values mapped to respective pieces of content in the memory.

In another embodiment, authentication levels for content may be stored in a DB of a server when user authentication (or iris authentication) is performed in the server.

Figure 17:
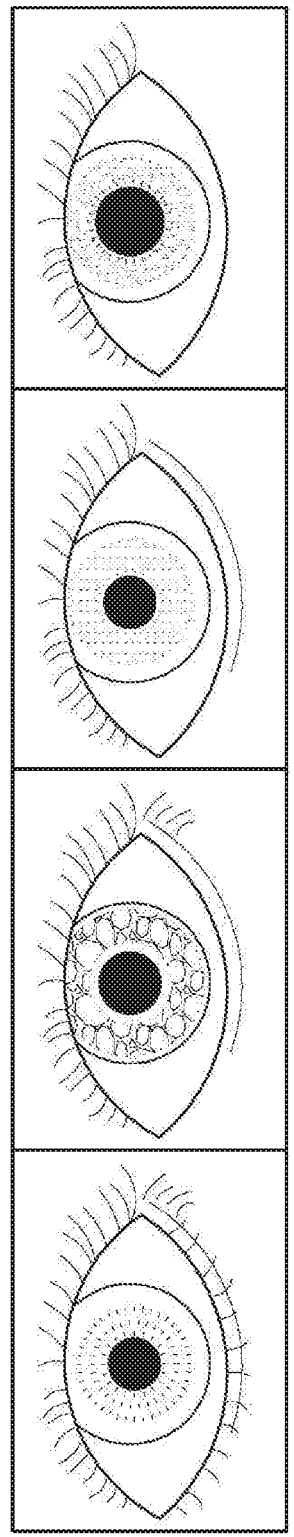
FIG. 17 shows boundaries of iris regions according to an embodiment of the present disclosure.

FIG. 17 shows boundaries of iris regions according to an embodiment of the present disclosure.

An iris image may also be used as a user's identification information. Based on the above-described method of detecting the boundary between the iris region and the sclera region, the iris region may also be used as identification information.

As shown in FIG. 17, every user has unique iris pattern, and a variety of identification methods using such iris patterns have been commercialized. Therefore, it is possible to improve the accuracy of user identification with a combination of an iris pattern and a capillary pattern.

Determination of a Fake Eyeball

Additionally, iris information may be used in combination with pulse information or so on. Existing iris information results from an iris pattern, and it is possible to copy iris information by drawing the iris pattern on a fake eyeball. Therefore, using a user's pulse information together with an iris pattern, it is possible to determine whether a fake eyeball is used.

At this time, the user's pulse information may be pulse information acquired through an analysis of the sclera region images described above with reference to FIG. 9. Alternatively, the user's pulse information may be pulse information transferred to the device through another route, such as the Internet.

FIGS. 18A to 18D show devices including an image acquisition unit according to an embodiment of the present disclosure.

The device described in embodiments of the present disclosure may be a device of various types, that is, a glasses type as shown in FIG. 18A or a smart phone type as shown in FIG. 18C. Any device capable of acquiring a user's eyeball image may be used without any limitation in its type.

In the case of the glasses type as shown in FIG. 18A, an image acquisition unit may be provided in the glasses as shown in FIG. 18B, and may include an illuminator. The device may analyze an image of reflected light which is emitted from the illuminator, and also perform an iris recognition function, a gaze-tracking function, and so on.

In the case of the smart phone type as shown in FIG. 18C, an illuminator, a visible light camera, etc. may be included on the front side or the rear side of the smart phone. The device may perform the iris recognition function, the gaze-tracking function, etc., and have two or more cameras on one side to perform the gaze-tracking function.

Embodiment 1—Acquisition of Biometric Information Using an IR Image Sensor

A device according to an embodiment of the present disclosure may acquire biometric information of a user corresponding to a subject using images captured by an IR image sensor. As described above with reference to FIG. 1, the device may analyze the images acquired from the IR image sensor to perform measurement of the user's pulse, user identification, determination of a fake eyeball, and so on.

Operations of the above-described device will be described below with reference to detailed embodiments.

(a) Pulse Measurement

Figure 19:
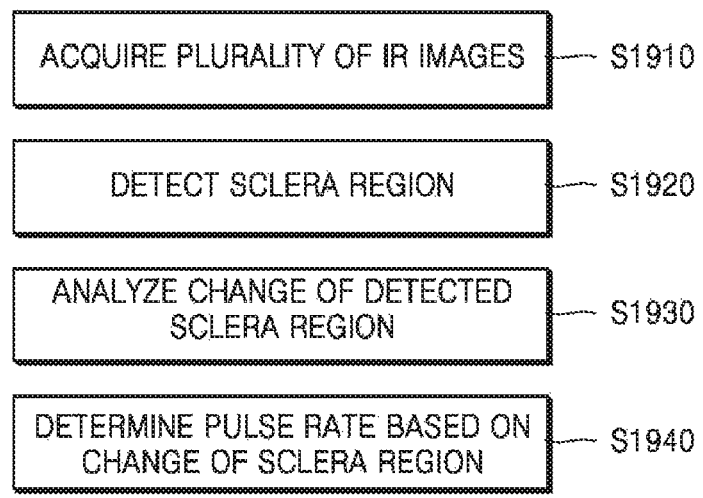
FIG. 19 is a flowchart illustrating a method of acquiring biometric information according to an embodiment of the present disclosure.

FIG. 19 is a flowchart illustrating a process in which a device determines a pulse rate using IR images according to an embodiment of the present disclosure.

The device may analyze images acquired from an IR image sensor to determine a user's pulse rate. Even in an environment in which there is no visible light, the IR image sensor may acquire an image by acquiring reflected IR light. Also, in the IR image, there is a significant difference in brightness between an iris and a pupil, and thus it is easy to detect a region outside the iris, that is, the sclera region, by detecting the iris region.

In operation S1910, the device may acquire a plurality of IR images. The plurality of IR images may be acquired by the IR image sensor embedded in the device, or images acquired by another IR image sensor separate from the device may be received through a wired or wireless communication network.

The plurality of images may be images acquired at regular time intervals. For example, four images may be acquired per second, or 30 images may be acquired per second. The time interval between the plurality of images is not limited to these examples, and it is also possible to acquire the plurality of images at irregular time intervals according to a user's setting.

In operation S1920, a controller of the device may detect a sclera region in the plurality of acquired images. In this case, the sclera region may be detected using the above-described method of FIGS. 5 and 6 or an iris recognition technology. Currently, there are many developed technologies for detecting the iris region or the sclera region, and any of them may be used.

In operation S1930, the device may analyze a change of the detected sclera region. The sclera region in the plurality of images may vary over time. An example of change information of the sclera region may be color information, bright information, capillary distribution (pattern) information, and so on.

A brightness change of the sclera region may be caused by contraction and expansion of capillary vessels. When blood flows through contracted capillary vessels, there may be little blood flow, and the capillary vessels may be brighter than the sclera region excluding blood vessels. When the capillary vessels expand, blood flow increases, and the capillary vessels may be darker than the sclera region excluding blood vessels.

Intervals of contraction and expansion of capillary vessels may be the same as intervals of the user's heartbeat, that is, such contraction and expansion of the capillary vessels may be proceeded according to the user's heartbeat.

In operation S1940, the device may determine a pulse rate of the user who is a subject based on the change information of the sclera region. By magnifying a difference in color, brightness, etc. of the sclera region, the controller of the device may facilitate detection of the difference. For example, the brightest image may be made brighter, the darkest image may be made darker, and a time interval between the brightest image and the darkest image may be calculated. When four images are acquired per second and the time interval between the brightest image and the darkest image is about 0.5 seconds, it is possible to determine that the brightest image is acquired every second and the user's pulse rate is about 60 beats per minute.

(b) User Identification

The device may use the plurality of acquired IR images as user identification information. Using pulse information of a sclera region and pattern information of capillary vessels, it is possible to identify a user. Alternatively, by detecting an iris region, it is possible to identify a user. The iris image varies according to the user and thus may be used as unique identification information.

The controller of the device may identify the user by combining identification information of the sclera region and identification information of the iris region. Because pulse information of the sclera region and pattern information of capillary vessels are user identification information and iris information also is identification information, it is possible to set different identification levels according to application executed in the device.

For example, for a simple function such as an unlocking of the device, only iris information may be necessary to identify the user, and for a financial function demanding a higher identification level than an unlocking of the device, it may be necessary to examine a matching of the user's pulse information or capillary pattern information as well as iris information. In this case, the user's pulse information or capillary pattern information within a predefined error level is sufficient. The controller of the device may also determine a fake eyeball in the same way as the user identification.

Embodiment 2—Acquisition of Biometric Information Using a Visible Light Image Sensor The device may acquire biometric information using a visible light image sensor. As described above, an IR image sensor is better for PPG application compared to a visible light image sensor. However, due to limited internal space and manufacturing costs of the device, biometric information may be measured using images acquired by the visible light image sensor.

The visible light image sensor of the device may acquire a plurality of images, which may be acquired at regular time intervals or time intervals set by a user. Alternatively, a fixed acquisition time may be given.

The controller may detect a sclera region in the acquired images. In a detected ocular region, a region excluding an iris region corresponds to the sclera region, and it is possible to detect the sclera region using various existing iris region detection methods. The following method has been described above with reference to operation S910 to operation S940, and the detailed description will not be reiterated.

Embodiment 3—Acquisition of Biometric Information Using a Visible Light Image Sensor The device may include both an IR image sensor and a visible light image sensor, and measure more accurate biometric information by analyzing images acquired by both the image sensors. Because the IR image sensor and the visible light image sensor may have different merits with respect to an environment in which the images are acquired, the controller of the device may use the IR image sensor and/or the visible light image sensor according to its surroundings.

Figure 20:
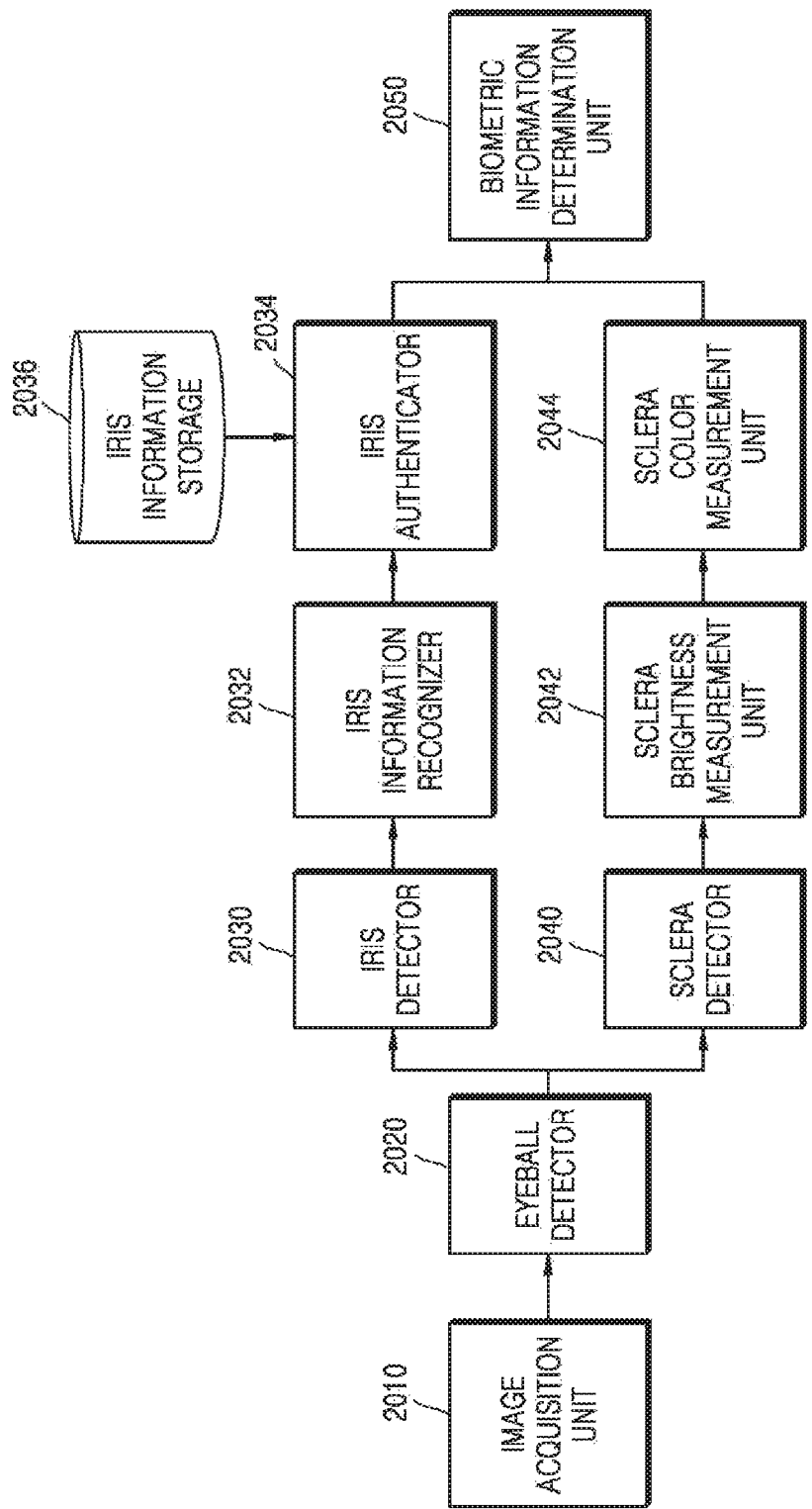
FIGS. 20 and 21 are block diagrams conceptually showing the structure of a device for acquiring biometric information according to an embodiment of the present disclosure.

FIG. 20 is a block diagram conceptually showing a structure of a device for acquiring biometric information according to an embodiment of the present disclosure.

The device described in this disclosure may include a configuration as shown in FIG. 20 to acquire information on an iris region and a sclera region. The device may include an image acquisition unit 2010, such as a camera, and an eyeball detector 2020 detecting an ocular region.

In FIG. 20, the eyeball detector 2020 may be included in a controller. The controller controls overall signal processing of the device, and thus the eyeball detector 2020 may be a module of the controller. Here, it is to be noted that a module may be a hardware module as a separate physical entity or a conceptual module classified as software.

Because an ocular region is generally divided into the iris region and the sclera region, the device may include an iris detector 2030, an iris information recognizer 2032, and an iris authenticator 2034. The iris authenticator 2034 may also receive iris information from an iris information storage 2036. Separate from the iris detector 2030, the device may include a sclera detector 2040 which detects the sclera region, a sclera brightness measurement unit 2042 which measures the brightness of the sclera region, and a sclera color measurement unit 2044 which measures the color of the sclera.

The device may include a biometric information determination unit 2050 which determines biometric information based on the above information.

Figure 21:
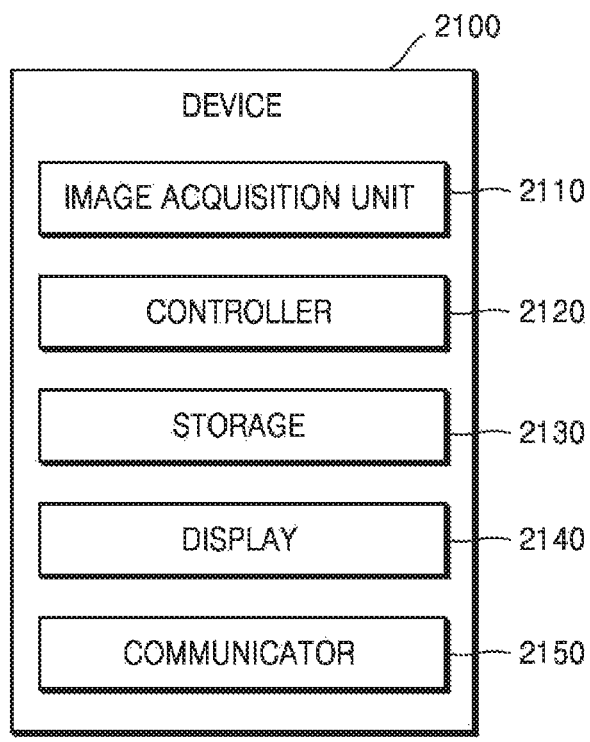

FIG. 21 is a block diagram conceptually showing a structure of a device for acquiring biometric information according to an embodiment of the present disclosure.

As shown in FIG. 21, a device 2100 may include an image acquisition unit 2110, a controller 2120, a storage 2130, a display 2140, and a communicator 2150.

The image acquisition unit 2110 may acquire a plurality of images including an ocular region as described above with reference to FIGS. 4 to 6. Also, the image acquisition unit 2110 may include an illuminator, which may include a visible light illuminator and/or an IR illuminator.

The controller 2120 may detect the ocular region in the images acquired by the image acquisition unit 2110. In this case, the controller 2120 may detect a facial region and then detect the ocular region. The controller 2120 may distinguish between the iris region and the sclera region, and detect an iris pattern in the iris region.

The controller 2120 may determine brightness and color information of the sclera region based on light emitted from the illuminator and reflected by the sclera region, and determine change information of the brightness and the color of the sclera region according to time based on images acquired at two or more points in time. The controller 2120 may determine biometric information, such as a pulse, etc., based on the determined change information.

The controller 2120 may perform a process of binarizing the determined change information. By performing the binarization process, the controller 2120 may rapidly and accurately make a comparison of the change information.

The storage 2130 may store data processed in or outside the device. The storage 2130 may store acquired images, and store iris images or sclera images which are usable as identification information.

The display 2140 serves to display details of processing carried out by the device, and the communicator 2150 may perform wired and wireless communication through interfaces in and outside the device.

Meanwhile, the above-described embodiments of the present disclosure may be written as a computer-executable program, and may be implemented in a general-purpose digital computer which executes the program using a computer-readable recording medium. Also, a data structure used in the above-described embodiments of the present disclosure may be recorded in a computer-readable recording medium using various tools. Examples of the computer-readable recording medium include storage media, such as magnetic storage media (e.g., a ROM, a floppy disk, a hard disk, etc.) and optically readable media (e.g., a CD-ROM, a DVD, etc.).

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A method for a device to acquire biometric information, the method comprising:

acquiring a plurality of images including an ocular region using an infrared ray (IR) image sensor;

detecting a sclera region in each of the plurality of acquired images;

sensing a change of the detected sclera region; and determining biometric information based on information on the sensed change of the sclera region, wherein the change of the sclera region includes at least one of a color change and a brightness change of the sclera region, and wherein the brightness change of the sclera region is caused by contraction and expansion of capillary vessels in the sclera region.

2. The method of claim 1, wherein the biometric information includes at least one of pulse information and distribution information of capillary vessels.

3. A non-transitory computer-readable recording medium storing a program for performing the method of claim 1 when the program is executed by a processor.

4. A device for acquiring biometric information, the device comprising:

an image acquisition unit configured to acquire a plurality of images including an ocular region using an infrared ray (IR) image sensor;

a storage configured to store the plurality of acquired images; and a controller, wherein the controller includes a sclera detector configured to detect a sclera region from each of the plurality of acquired images, and is set to sense a change of the detected sclera region and determine biometric information based on information on the sensed change of the detected sclera region, wherein the change of the sclera region includes at least one of a color change and a brightness change of the sclera region, and wherein the brightness change of the sclera region is caused by contraction and exansion of capillary vessels in the sclera region.

5. The device of claim 4, wherein the controller comprises an eyeball detector, and the eyeball detector comprises:

an iris detector configured to detect an iris region in the plurality of acquired images; and the sclera detector.

6. The device of claim 5, wherein the controller is set to identify a user based on a pattern of the detected iris region.

7. The device of claim 6, wherein the controller is set to determine the biometric information based on the information on the sensed change of the sclera region and binarize the information on the sensed change of the sclera region.

8. The device of claim 4, wherein the biometric information includes at least one of pulse information and distribution information of capillary vessels.

9. The device of claim 4, wherein the contraction and expansion of the capillary vessels in the sclera region are changes repeated at identical time intervals to a heartbeat of a user having the sclera region.

10. The device of claim 4, wherein the controller detects the ocular region in the plurality of acquired images including the ocular region, and the sclera detector is set to detect the sclera region in the detected ocular region.

11. The device of claim 4, wherein the controller is set to detect a gaze of a user in the plurality of acquired images.

* * * * *